(12) United States Patent
Lumbroso et al.

(10) Patent No.: US 7,921,810 B2
(45) Date of Patent: Apr. 12, 2011

(54) METHOD AND APPARATUS UTILIZING ANIMALS FOR DETECTING TARGET SUBSTANCES

(75) Inventors: Eran Lumbroso, Herzlia (IL); Alon Lumbroso, Bnei-Zion (IL)

(73) Assignee: Bio Explorers Ltd., Herzlia (IL)

( * ) Notice: Subject to any disclaimer, the term of this patent is extended or adjusted under 35 U.S.C. 154(b) by 233 days.

(21) Appl. No.: 12/085,021

(22) PCT Filed: Nov. 19, 2006

(86) PCT No.: PCT/IL2006/001328
§ 371 (c)(1),
(2), (4) Date: May 15, 2008

(87) PCT Pub. No.: WO2007/057901
PCT Pub. Date: May 24, 2007

(65) Prior Publication Data
US 2009/0145369 A1 Jun. 11, 2009

Related U.S. Application Data

(60) Provisional application No. 60/597,249, filed on Nov. 18, 2005.

(51) Int. Cl.
*A01K 1/03* (2006.01)
(52) U.S. Cl. ...................................................... 119/421
(58) Field of Classification Search .................. 119/417, 119/421, 221, 472, 473; 340/573.1
See application file for complete search history.

(56) References Cited

U.S. PATENT DOCUMENTS

| | | | | |
|---|---|---|---|---|
| 3,100,473 A * | 8/1963 | Kissel | ............................ | 119/421 |
| 3,540,413 A * | 11/1970 | Castaigne | ...................... | 119/421 |
| 3,693,590 A * | 9/1972 | Bowers | ......................... | 119/421 |
| 3,974,798 A * | 8/1976 | Meetze, Jr. | ..................... | 119/421 |
| 4,022,054 A * | 5/1977 | Biederman | ................... | 73/23.34 |
| 4,917,046 A * | 4/1990 | Spengler | ....................... | 119/420 |
| 4,968,974 A * | 11/1990 | Sakano | ........................ | 340/573.3 |
| 4,969,417 A * | 11/1990 | Sakano | .......................... | 119/421 |
| 5,608,209 A * | 3/1997 | Matsuda | ........................ | 250/221 |
| 6,715,444 B1 * | 4/2004 | Yabusaki et al. | ............... | 119/421 |
| 6,825,768 B2 * | 11/2004 | Stapelfeld et al. | .......... | 340/573.3 |
| 6,843,158 B2 | 1/2005 | Garcia et al. | | |
| 2001/0047771 A1 | 12/2001 | Bulanda et al. | | |
| 2003/0083822 A2 | 5/2003 | Brunner et al. | | |

FOREIGN PATENT DOCUMENTS
WO    WO 01/92850    12/2001

OTHER PUBLICATIONS

International Search Report Dated Oct. 27, 2008 From the International Searching Authority Re.: Application No. PCT/IL06/01328.
Written Opinion Dated Oct. 27, 2008 From the International Searching Authority Re.: Application No. PCT/IL06/01328.
Office Action Dated Jul. 28, 2010 From the Israel Patent Office Re. Application No. 191522 and Its Translation Into English.

* cited by examiner

*Primary Examiner* — Rob Swiatek
*Assistant Examiner* — Ebony Evans (57) ABSTRACT

A method and apparatus for detecting a target substance in a monitored environment involves, in a training phase, training at least one animal capable of detecting the target substance to execute a particular avoidance action, immediately upon detecting said target substance, in order to avoid particular aversive stimulus;
and in an operational phase, exposing the trained animal to a specimen (e.g., air) from the monitored environment or object, and sensing when the animal has executed the particular avoidance action.

14 Claims, 4 Drawing Sheets

METHOD AND APPARATUS UTILIZING ANIMALS FOR DETECTING TARGET SUBSTANCES

RELATED APPLICATIONS

This Application is a National Phase of PCT Patent Application No. PCT/IL2006/001328 having International filing date of Nov. 19, 2006, which claims the benefit of U.S. Provisional Patent Application No. 60/597,249 filed on Nov. 18, 2005. The contents of the above Applications are all incorporated herein by reference.

FIELD AND BACKGROUND OF THE INVENTION

The present application relates to a method and apparatus utilizing animals for detecting target substances, such as trace particles, odors and vapors. The invention is useful in many applications, for example in detecting explosives, narcotics or other controlled substances, rotten food products, pesticide residues, chemical by-products of medical situations, etc.

Many techniques have been developed for detecting target substances, e.g., as target odors, present at extremely low concentrations, e.g., in the order 1 part per million, or less. Trained canines have probably been used more than any other method for the detection of explosives under real-world conditions. An animal's nose is the best sensor that evolution has to offer, and it competes favorably with man-made detection technologies under many circumstances. At the present time, there is no mechanical device as accurate, fast, sensitive, mobile, flexible and durable as a well-trained dog/handler team.

However, there are a number of disadvantages in using canines as explosive detectors. First and foremost, adequately maintaining a canine operation, especially in the one-handler-to-one-dog mode preferred by many law enforcement organizations, is very expensive. Costs include initial acquisition of the animals, training for both the dog and the handler, veterinary and other maintenance expenses for the dogs, and the salary and other expenses associated with the handler, this last constitutes the largest fraction by far.

Thus, explosive sniffer dogs do not, and cannot, operate by themselves. They always function in tandem with their handler. The leash that connects the man and dog is not so much a means of control as a channel for communication. This is both a strength and a weakness. When a team is in top form, the dog and his handler function with amazing efficiency. But the dog works only as well as his master. Security searches are frequently boring, monotonous chores, the sort of tasks for which humans have trouble staying alert. If the dog senses a lack of commitment on the part of his human teammate, the dog's effort similarly diminishes. Also, it is inaccurate to say that the dog finds the explosive. It is up to the handler to recognize the sometimes-subtle changes in the dog's behavior that signal interest in a faint scent. This reliance on the handler's judgment introduces a second possibility of error.

Dogs have a number of weaknesses when compared to mechanical sniffer devices. Being a live creature, dogs cannot be worked as intensely as a piece of machinery. Depending on temperature and humidity conditions, a dog may be able to work only about 20 minutes before he needs a rest. Dogs are also vulnerable to distraction by loud noises, bright lights, new surroundings, fatigue, and alluring scents left behind by canines of the opposite sex. Dogs have a limited attention span. They cannot be positioned beside a conveyor belt, even under comfortable conditions, and be expected to sniff luggage effectively hour after hour. They must be actively engaged in the search, or their acuity will sharply diminish. They also are prone to personality quirks. Some dogs refuse to go in glass elevators; some will not fly in helicopters; some bond very strongly to their handlers, while others are more aloof.

The use of other animals with a developed sense of scent to detect volatile materials is also well known in the art, and is described, among other places in Biederman U.S. Pat. No. 4,022,054.

In most of the methods known in the art, animals are trained by positive reinforcement to actively search for and find the source of the scents typical to the relevant type of material. The animals are then brought to a suspicious place and are instructed to seek the scent, motivated by the expected reward, However, positive reinforcement training and operation carries some inherent limitations that negatively affect their affectivity:

1. The animal will not perform when it is satiated
2. The animal is trained for short term missions and cannot perform continuous monitoring
3. With canines, the operation of the animal typically requires a human trainer or operator and cannot be performed unattended
4. The animal needs frequent training with the target material and reward in order to keep low false alarm rate and high detection rate.

These limitations are problematic both in the operational and in an economical sense.

OBJECTS AND BRIEF SUMMARY OF THE PRESENT INVENTION

An object of the present invention is to provide a method and apparatus utilizing animals for detecting target odors but having advantages in many respects over the previously-known methods, as will be described more particularly below.

According to one aspect of the present invention, there is provided a method of detecting a target substance in a monitored environment or object, comprising: (a) in a training phase, training at least one animal capable of detecting the target substance to execute a particular avoidance action, immediately upon detecting said target substance, in order to avoid a particular adverse stimulus;

and (b) in an operational phase, exposing the trained animal to a specimen of the monitored environment or object, and sensing when the animal has executed the particular avoidance action.

It will thus be seen that the method of the present invention is not based on positive reinforcement, wherein the animal receives a reward when detecting a target odor and manifests a particular behavior to indicate this to the handler. Rather, the method of the present invention is based on an avoidance behavior involving negative reinforcement, wherein the animal, upon detection of the target substance, is trained to perform a specific avoidance action in order to avoid receiving an adverse (e.g., irritating) stimulus. Such a method is therefore not subjected to the limitations and problems involved in positive reinforcement training, as previously discussed above.

The method of the present invention is also to be sharply distinguished from that described in the above-cited Biederman US Pat. No. 4,022,054. In that patent, during the training phase the animal is given an electrical shock when exposed to the monitored substances, and is trained to depress a first lever to terminate the shock if the target odor is detected, or to depress a second lever to terminate the shock if no target odor is detected. Thus, in that method, the adverse stimulus (electrical shock) is applied at each discrete check, and is terminated only if the animal selects the proper lever to depress. In the method of the present invention, however, the adverse stimulus is not applied to the animal unless the animal, upon detecting the target odor (or other target substance), does not immediately execute the particular avoidance action. Moreover, in the operational phase of US Pat. No. 4,022,054, the adverse stimulus is administered in each and every check (of a person or object) and terminated only upon a correct lever press (this will, of course, limit the possible frequency of checks), whereas in the present invention the adverse stimulus is given only at the training phase and only if the animal fails to detect a target odor.

Preferably, the particular avoidance action is one which the animal would normally not perform under normally—existing conditions, i.e. when the target odor is not detected. In the described preferred embodiment, the particular avoidance action is to move to a "safe" section of the cage which is accessible to the animal only with some difficulty. For example, the "safe" section of the cage could be one requiring a relatively steep ascent or descent, a restricted passageway, or a confined space (e.g., tunnel), to be remembered by the animal as a "safe haven" to move to when detecting the target odor, in order to avoid the adverse stimulus.

The particular adverse stimulus may be an electrical, audible, visual, thermal or mechanical stimulus, such as an electrical shock, a loud sound, bright light, heat or mechanical vibration, which the animal naturally wishes to avoid.

According to further features in the described preferred embodiment, during both the training phase and the operational phase, the animal is housed within a cage including the basic living necessities for the animal, i.e. food, water, exercising device, etc. Preferably, during at least the operational phase, the cage includes a plurality of animals, each trained to detect the target substance, e.g., the target odor. All the animals may be trained to detect the same target substances and to perform the same avoidance action. On the other hand, one or more of the animals may be trained to detect different target substances and/or to perform a different avoidance action, from the others.

The invention thus provides:

a method where no reward like food, water, electric brain stimulation or other is given following the detection.

a method where no stimulation other than the inspected object precedes the detection decision.

a method where the detection reliability is increased by using a social group of animals that are cooperating or at least by using sufficient number of animals to increase the probability that few of them will detect the target material at each check; and a method where the shift duration is increased by using a social group of animals that are cooperating and sharing the alertness time synergically or at least by using sufficient number of animals to increase the probability that few of them will be awake and alert at all times.

Such an arrangement has a number of advantages. First, it better assures that there will be at least some alert animals at all times. In addition, employing a plurality of animals increases the probability that a target odor will be detected. Assuming that the alarm occurs only if a predetermined number of animals execute the avoidance behavior, it also reduces the probability of a false alarm, i.e. which may occur when one animal falsely manifests the detection of the target odor, whereas others do not. Further, it enables, in one operation using one device, to discriminate and identify different target odors. One animal can also be trained to detect many target odors.

According to further features in the described preferred embodiment, during the operational phase, a target odor may be occasionally injected into the cage to verify the ability of the animal to detect the target substance. In addition, during the operational phase, a neutral substance may also occasionally be injected into the cage to verify the ability of the animal to distinguish between neutral substances and target substances.

According to further features in the described preferred embodiment, during the training phase, an alerting stimulus may be produced immediately after the exposure of the animal to the target substance in order to facilitate the conditioning of the animal. Also, during the training phase, a "safety" stimulus may be produced immediately after sensing the avoidance action.

The animals may be of the same species, or of a different species, and may be selected from the group consisting of rats, mice, dwarf hamsters, gerbils, shrews, dogs, monkeys, birds, insects and fish.

According to another aspect of the present invention, there is provided apparatus for training animals to detect a target substance in a monitored environment in accordance with the above method.

Further features and advantages of the invention will be apparent from the description below.

BRIEF DESCRIPTION OF THE DRAWINGS

The invention is herein described, somewhat diagrammatically and by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

Figure 1:
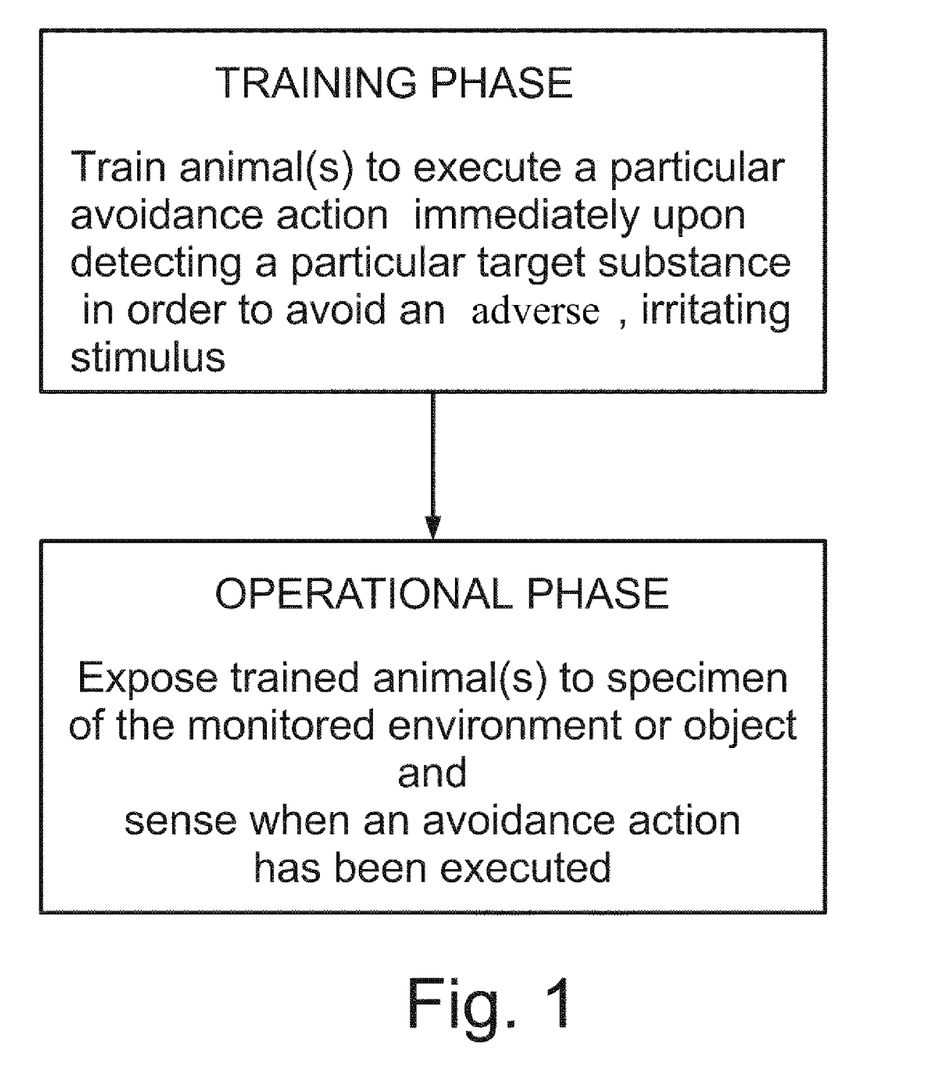
FIG. 1 is a block diagram illustrating the overall method utilizing animals for detecting a target substance in a monitored environment, namely, the training phase and the operational phase.

FIG. 1 is a block diagram illustrating the two phases in the overall method, namely the training phase wherein one or more animals are trained to execute an avoidance action immediately upon detecting a particular target substance in order to avoid an aversive stimulus; and the operational phase, involving exposing the animal or animals to a specimen of the monitored environment, and sensing when an avoidance action is executed by the animal or animals. In most cases, the animal or animals would be land animals or birds, in which case the target substances would be target odors in the monitored environment, and the invention is therefore described below with respect to such an application. It is contemplated, however, that the target substances to be detected may be substances of extremely low concentration in a body of water, in which case fish could be trained in accordance with the present invention to detect such a target substance.

Figure 2:
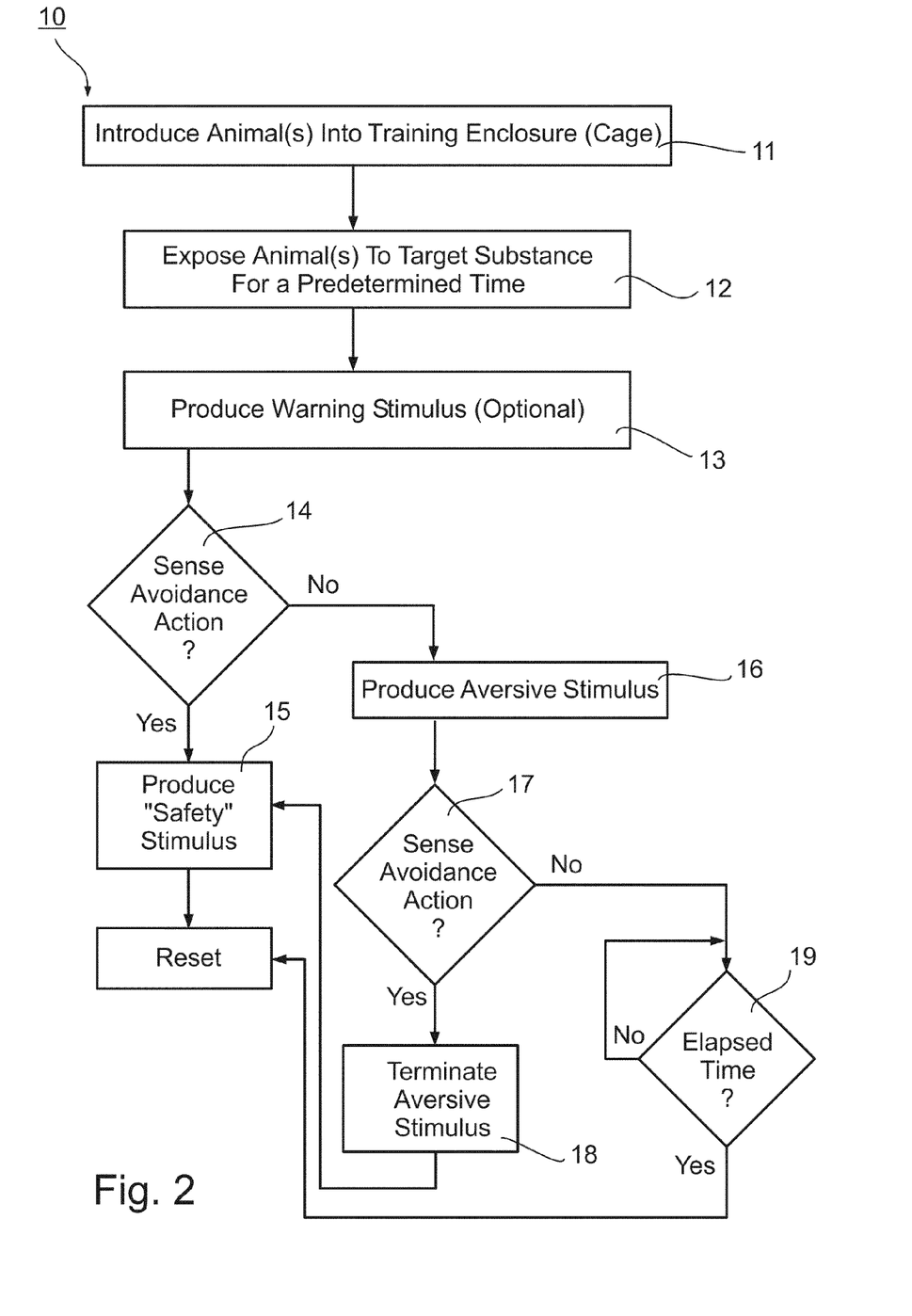
FIG. 2 is a flowchart illustrating the training phase in the described preferred embodiment of the invention.
Figure 4:
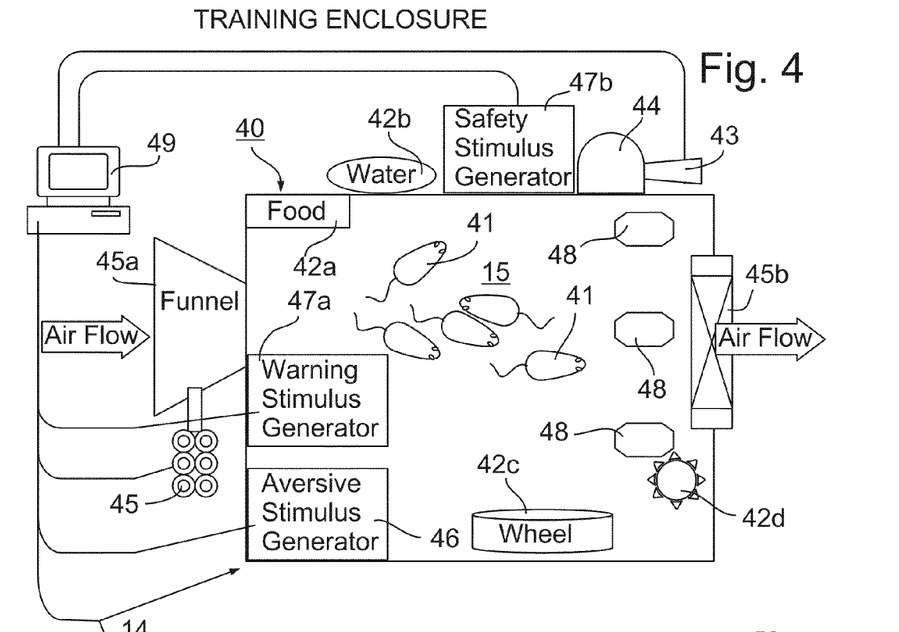
FIG. 4 is a block diagram illustrating an example of a training enclosure, e.g., cage, used during the training phase.

FIG. 2 is a flow diagram illustrating an example of an avoidance behavior training process in which one or more animals are trained, through negative reinforcement, to perform a specific action, upon the detection of the relevant target substances (or target odors), in order to avoid receiving an aversive stimulus which is particularly unpleasant to the animal or animals. The training process is effected in a number of training sessions, as follows:

1. In the first training sessions, the animal or animals are introduced into the training enclosure (cage), e.g., as shown in FIG. 4, which includes the basic living necessities for the animal, such as food, water, exercising devices, and the like. At this stage, the animal or animals are exposed to the normal environmental conditions including air movement, different neutral odors, noises, and the like, existing in the environment to be eventually monitored. The enclosure would include a "safe haven", as described above, to which the animal is trained to go when detecting a particular target odor, in order to avoid the aversive stimuli.

The next sessions constitute the conditioning sessions, to condition the animal or animals to respond to particular target odors by executing a particular avoidance action (e.g., entering the "safe haven") in order to avoid a particular aversive stimulus. Each conditioning session includes the following operations:

(a) expose the animal (or animals) to the target odor (block 12);

(b) after a predetermined time delay (e.g. a few seconds), optionally produce an alerting stimulus (e.g. energize a light, generate a sound, etc);

(c) within a predetermined time period (e.g. a few seconds) determine whether the sensor has been actuated showing that the animal executed the avoidance action (block 14);

(d) if the sensor was actuated to indicate this, produce a "safety" stimulus (e.g. another light or sound) to confirm to the animal that it is "safe" from the aversive stimulus (block 15), terminate target odor injection and then reset the apparatus;

(e) if, on the other hand, it was determined (in block 14) that the animal did not execute the avoidance action within the permissible time period (e.g. a few seconds), produce an aversive stimulus which is particularly unpleasant to the animal, such as electrical shock, a loud noise, a bright light, thermal heat, or mechanical vibration (block 16);

(f) continue to sense whether the animal executes the appropriate avoidance action (block 17), and if so, terminate the aversive stimulus (block 18), terminate target odor injection, produce the safety stimulus (block 15), and then reset;

(g) if, however, after the expiration of a predetermined time period (e.g. 5-10 seconds), no avoidance action is sensed, then reset the system.

2. Each conditioning session includes a plurality of the above sequential operations (trials), separated by time intervals of seconds to minutes, increasing gradually as training progresses. During these intervals the animals are exposed to neutral odors which are not followed by any other stimulus. The number of sequential operations (trials) per session may range from a few to tens.

3. The particular avoidance behavior of the animal or animals may be shaped by small approximations towards the final expected behavior, or may be required from the first trial, depending on the complexity of the behavior. Initially the animal responds to the aversive stimulus—escapes from the aversive stimulus to the "safe haven". Then the response of the animal gradually becomes faster and earlier until it precedes the aversive stimulus, and then precedes the possible alerting stimulus. Thus, the animal avoids the aversive stimulus by detecting the target odor (executing the particular avoidance behavior).

Gradually, the probability of avoidance (detection) increases, and the probability of escape/miss/false negative decreases.

After the avoidance behavior is stable (detection rate >80%), the odor concentration should gradually be decreased until reaching a concentration where the probability for detection is 50%.

If desired, new target odors may be introduced in subsequent sessions. The introduction of each new target odor should be followed by the optional warning stimulus followed by the aversive stimulus if the correct response is not executed, and by the "safety" stimulus if the correct response is executed. Additional neutral odors may also be introduced in subsequent sessions, in which case there would be no aversive stimulus, or alerting stimulus following the introduction of the odor, or "safety" stimulus following a response.

The animals may be trained individually or as a group. The reaction time of the animals would be expected to vary according to the particular animal and the degree of training. The performance of the individual animals in the group may be monitored (e.g., by video, RFID (radio frequency identification devices)) or other method. Substandard performers may be withdrawn from a group for further individual training, or removed altogether from the group.

Gradually, the concentration of the target odors may be decreased, and the number of target odors, the number of neutral odors, and the session durations may be gradually increased. The false alarm rate can be reduced by increasing the difficulty of the behavior, and/or by increasing the exposure of the animals, to the false causing odors.

The training period should preferably continue for each animal until the animal responds to the trigger, quickly and repeatedly. When an animal fails to do this, the animal should be dropped from the group. In the course of training, the performance of each individual animal can be monitored, and best performers can be used for breeding, thus improving the next generations of the population.

Each animal can be trained for a particular target odor or for a plurality of target odors. In addition, each animal can be trained to execute the same avoidance action, or a different avoidance action. For example, if one or more of the animals in a cage are trained to detect a different target odor from one or more of the others, and to execute a different avoidance action from the others, the system will be able to identify the presence of different target odors.

If the scent of the relevant target odor is similar to the scent of a neutral, irrelevant target odor, there is a risk that the animal, in case of doubt, will also respond to the non-relevant odor. The training sessions can specifically address this possibility by introducing the non-relevant (neutral) target odors very gradually from low to high concentrations, introducing them for relatively long times, alternating the relevant and non-relevant target odors frequently, and ignoring the responses to the non-relevant target odors. The animal is thus trained to detect the relevant target odors but not to respond to decoys or to similar odors.

Figure 3:
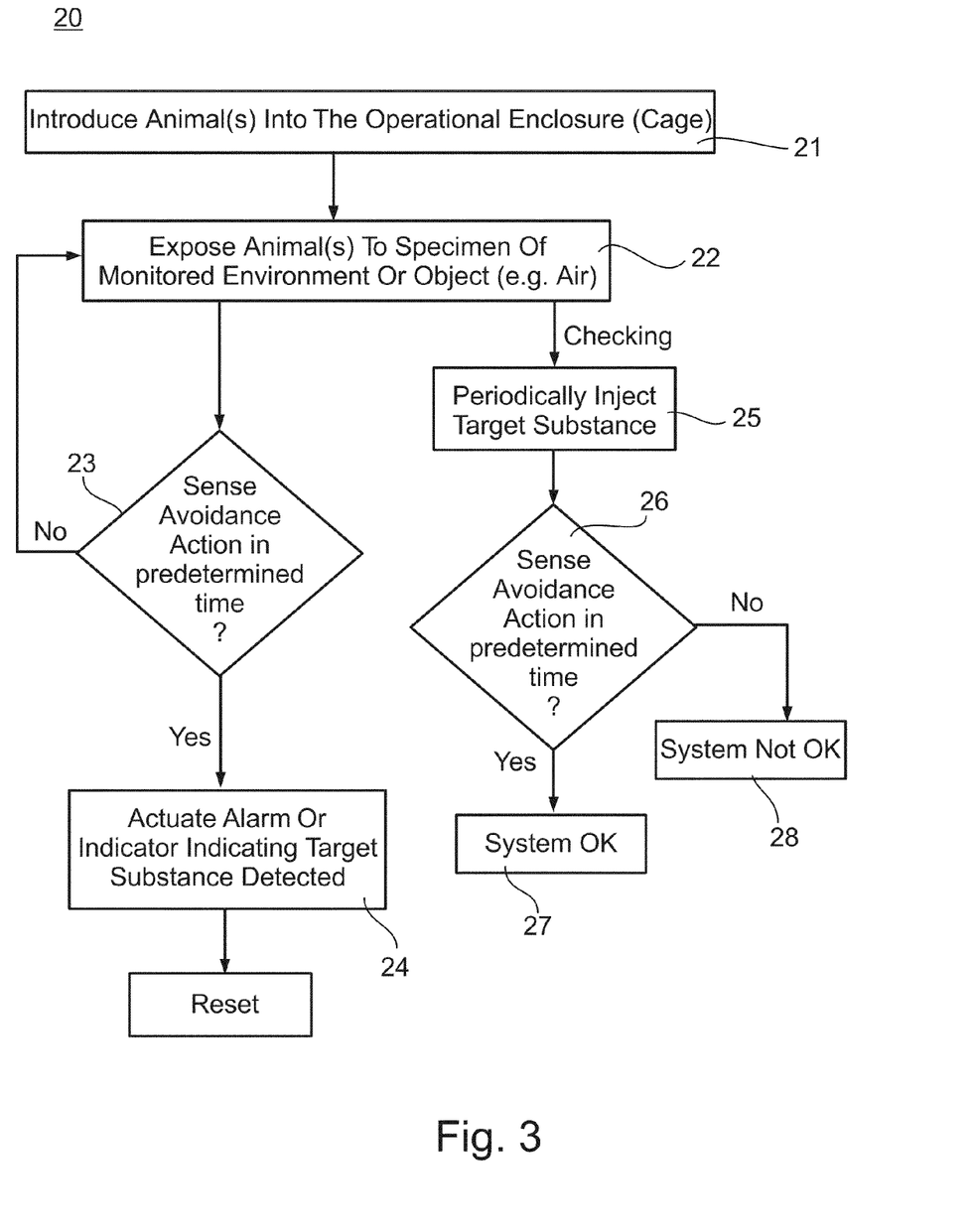
FIG. 3 is a flowchart illustrating the operational phase in the described preferred embodiment of the invention.

FIG. 3 is a flow chart illustrating an example of the operational phase, wherein the trained animal or animals are exposed to specimens of the monitored environment, and wherein whether or not an avoidance action has been executed, is sensed.

Figure 5:
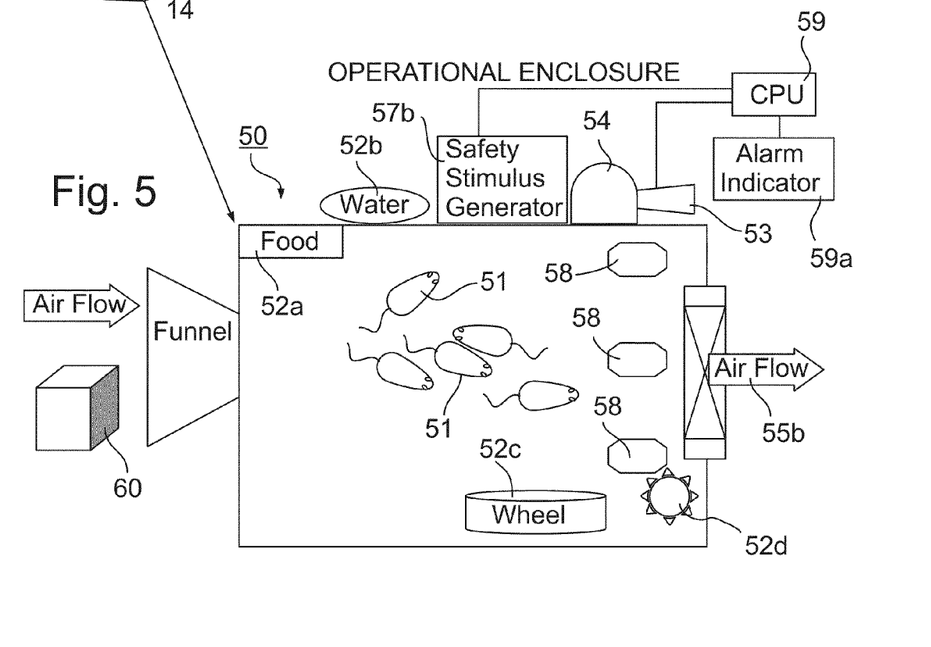
FIG. 5 is a block diagram illustrating an example of an operational enclosure, e.g., cage, used during the operational phase.

Thus, as shown in the flowchart of FIG. 3, the trained animals are introduced into the operational enclosure (cage) such as illustrated in FIG. 5 (block 21, FIG. 3).

The cage, with the animals therein, is then placed in the monitored environment so as to expose the animals to the air in the monitored environment (block 22).

Whenever an avoidance action executed by the animals is sensed, by the operation of a sensor for this purpose, an indicator or other signal is actuated to thereby indicate that a target odor was sensed to be present in the monitored environment (blocks 23, 24).

It is preferable to check the proper operation of the system by injecting a target odor into the cage (block 25) at pre planned times and sensing whether an avoidance action has been taken by the animals (block 26). If an avoidance action has indeed been taken, an indicator can be energized to indicate the system is working satisfactorily (block 27); but if no avoidance action is sensed, this would indicate that the system is not operating satisfactorily (block 28), and therefore should be checked or replaced by a proper system.

If desired, the system could also be checked by injecting small amounts of a similar, but neutral (i.e., not relevant) odor, and verifying that no output signal is produced showing that an avoidance action has not been taken.

An operational system may include more than one enclosure, either for redundancy (same training in each enclosure), for diversity (different training in each enclosure), or for covering longer detection shifts. The vigilance of at least some of the animals in the enclosure at all times can be assured by artificially and periodically awakening part of the animals. This may be done by generating arousal stimulations in a particular section of the enclosure that arouse the animals occupying the respective section without disturbing the animals sleeping in other parts of the enclosure. Such arousal stimulations can be floor vibration, floor temperature variations, weak voltage differences across the floor, changing of lighting conditions, production of airflow through a specific section of the enclosure, etc.

The detection system may function as a standalone alarm for detecting the presence of the target odors, or may be integrated into a security terminal producing outputs delivered to a control center and/or a support center. The system may also be used to examine baggage/cargo by vacuuming the air in it and bring it to the enclosure.

The operational enclosures may be constructed as changeable cassettes that fit into a complete detection system. Each cassette may include a group of trained animals and the basic living conditions for about 1-4 weeks. Once every 1-4 weeks the deployed enclosures may be replaced by fresh enclosures, and the previously-used enclosures may be taken back to a service facility for servicing, cleaning and replenishing with new food, water and bedding. The animals may also be checked for their health and detection performance, and, if appropriate, given refreshment training in order to bring their avoidance behavior to optimal performance towards their next assignment.

FIG. 4 schematically illustrates a training enclosure that may be used during the training phase, and FIG. 5 schematically illustrates an operational enclosure that may be used in the operational phase.

The training enclosure illustrated in FIG. 4, and therein designated 40, is in the form of an open cage, of a size suitable for accommodating a plurality (e.g. 4-8) of small animals 15, such as mice, gerbils or other animals, capable of detecting the target odors desired to be detected. The enclosure may be divided to several separate cells, each containing a single animal or a small group of animals. The cage is provided with the basic living necessities for the animals, including food 42a, water 42b, exercising device 42c and lighting device 42d. Cage 40 is also provided with "safe haven" 44, or a plurality of such "safe havens", one for each animal 41, to which the animal would be conditioned to move, upon sensing the target odor, by avoidance behavior training, that is, in order to avoid an aversive stimulus upon detecting the target odor. Each such "safe haven" may be a section of the cage which is accessible to the animal only with some difficulty, and therefore to which the animal would not intentionally move in the absence of detecting a target odor. For example, each "safe haven" 44 may be a section of the cage accessible only by stepping upwardly, or by passing through a restricted passageway, or be a confined space such as a tunnel. Each such "safe haven" 44 would include a sensor 43 which senses the movement of an animal to the "safe haven" 44, and actuates an electrical signal in response thereto.

The training enclosure 40 illustrated in FIG. 4 further includes an odor injector 45, for selectively injecting target odors as well as neutral odors, to be used in the training process. The odor or odors are injected by injector 45 into an air stream passing through a funnel 45a at one end of the enclosure, and drawn through the enclosure by a fan 45b at the other end.

Training enclosure 40 further includes an aversive stimulus generator 46, for generating an aversive stimulus, such as electrical shock, a loud noise, bright light, thermal heat, or mechanical vibration, which is highly unpleasant to the animals 41 within the cage and which the animals are to be trained to avoid by executing a particular avoidance action, in this case quickly moving to a "safe haven" 44. Training enclosure 40 may further include a warning stimulus generator 47a, to generate a stimulus immediately after the exposure of the animal to a target odor from injector 45. Training enclosure 40 further includes a safety stimulus generator 47b, which is actuated if sensor 43 is actuated and target odor is on. The safety stimulus will confirm to the animal that the appropriate avoidance action was taken and no aversive stimulus is expected.

Training enclosure 40 may further include one or more arousal stimulus generators 48 at one section of the cage. These are periodically actuated to arouse any of the animals occupying that section of the cage, and thereby to assure at least some of the animals will be awake at all times for detecting the target odor. Alternatively, the air flow, containing the specimen may shift between sub-units of the system, thus keeping one subunit alert while the other is resting Finally, the training enclosure 40 illustrated in FIG. 4 includes a computer controller 49 which controls and monitors all the training process: injecting the target and neutral odors by actuation of the odor injector 45, actuating the warning stimulus generator 47a and the aversive stimulus generator 46 if sensor 43 is not actuated on time to indicate that the proper avoidance action was taken by the animal upon detecting the target odor, actuating the safety stimulus generator 47*b* if sensor 43 is actuated on time and collecting all the training and performance parameters of the training sessions The operational enclosure illustrated in FIG. 5, and therein designated 50, could be of basically the same construction as the training enclosure 40 illustrated in FIG. 4, except that certain elements are not essential and therefore could be omitted, namely the odor injector 45, the aversive stimulus generator 46, and the alerting stimulus generator 47*a*. Thus, the operational enclosure 50 of FIG. 5 may also be an open cage of similar structure as the cage in the training enclosure 40 of FIG. 4. It should be constructed of sufficient size to accommodate a plurality of small animals 51 (corresponding to animals 41 in FIG. 4 after their training), and the basic living necessities for the animals, including a source of food 52, a source of water 52*b*, exercising device 52*c* and lighting device 52*d*. Operational enclosure 50 would also include one or more safe havens 54 and sensors 53, corresponding to elements 43 and 44 in the training enclosure 40 of FIG. 4. The animals within enclosure 50 are exposed to the air from the monitored environment via funnel 55*a* at one end of the enclosure, as forced through the enclosure by a fan 55*b* at the opposite end. A section of enclosure 50 further includes one or more arousal stimulus generators 58, corresponding to 48 in FIG. 4, for periodically arousing the animals occupying that section of the cage, and thereby better assuring that at least one or more of the animals will always be awake for detecting target odors. Alternatively, the air flow, containing the specimen may shift between sub-units of the system, thus keeping one subunit alert while the other is resting Finally, the operational enclosure 50 illustrated in FIG. 5 includes a processor 59 which, monitors the multiple sensors 53, and controls the safety stimulus generator 57*b* and the alarm 59*a*. The processor 59, receives the outputs from the different sensors 53, produces a weighted resultant decision and actuates the alarm 59*a* and the safety stimulus generator 57*b*, accordingly, thereby increasing the detection rate and reducing the false alarm rate of the decision that a target material has been detected. Control center notification and/or control of other hardware such as locking a turnstile (not shown) may be performed in parallel to actuation of alarm 59*a*.

For purposes of example, FIG. 5 illustrates the operational enclosure 50 as exposed to air flowing over or through a container 60 containing a specimen odor to be examined.

It will be seen that sensor 43 in the training enclosure of FIG. 4, or 53 in the operational enclosure of FIG. 5, translates the animals acts of avoidance behavior into a useful output signal. In the preferred embodiments illustrated in FIGS. 4 and 5, the avoidance behavior performed by the animal is to move into a section of the enclosure (44, FIGS. 4 and 54, FIG. 5) which is accessible to the animal only with some difficulty. However, the sensors 43 and 53 may be designed to sense other avoidance behaviors of the animal in order to avoid the unpleasant aversive stimulus when detecting a target odor, such as changing the ordinary rate of motion of the animal, making a detectable sound, moving to another specific location in the enclosure, making contact with a specific device in the enclosure, making a body gesture that is visually noticeable, changing its heart rate, or changing the relationship to other animals in the enclosure.

The sensor that recognizes the avoidance behavior and creates an output signal may be one of the entries in the following Table 1.

TABLE 1

| Transducer | Detectable behavior | Signal pre-processing |
| --- | --- | --- |
| Light beam interruption | Presence of animal in a specific location | Duration of interruption |
| Microswitch change of state | Force applied by animal on a specific item | Duration of temporary state |
| Capacitance detection | Contact or proximity of animal to a specific conductor | Duration and level of change in capacitance |
| Video image interpreter | Body dynamics of the animal | Image processing and pattern recognition |
| Microphone | Production of sounds by animal | Bandpass filtering, amplification and detection |
| Piezoelectric transducer | Body motion dynamics | Bandpass filtering, amplification and detection |
| Heart rate transmitter | Changed heart rate | Bandpass filtering, amplification and detection |

The signal that can be produced by the sensor is used to notify a host system of the detected presence of a target odor or other target substance. The notice may be a local visual or audio indication to an operator, or an analog or digital report communicated by wire or wireless to a remote processing system such as a computer. The notice may be delivered to a local pre-processor that processes the notice together with other signals coming from the same and other sensors over a period of time, in order to produce a weighted resultant decision, thus increasing the reliability and reducing the false alarm rate of the decision that a target substance has been detected.

The appearance of one instance of an avoidance action may be considered as enough to declare the present of a target substance, or multiple instances of the avoidance acts may be required before the presence of a target substance is declared.

The described method and apparatus may be used in a variety of applications where there is a need for detection of very small quantities of molecules released to the air from a volatile material. Following Table 2 includes examples of such applications:

TABLE 2

| Application | Scene | Volatile materials | Need |
|---|---|---|---|
| People screening | Mass transit, high risk facilities, crowded environments, border customs | Explosives, narcotics | Terror act prevention |
| Cargo inspection | Ports, cargo terminals | Explosives | Terror act prevention |
| Perimeter security | Gates and entrances to secured facilities | Explosives | Terror act prevention |
| Agricultural products inspection | Inspection points | Rotten merchandise, pesticide residues | Enforce agricultural regulations |
| Border customs and police stations | Crime scenes | Narcotics, explosives | Law enforcement |
| Medical diagnosis | Hospitals, clinics | Chemical by-products of medical situations | Early detection of disease |
| Quality of food inspection | Customs, agricultural control points | Pesticides | Detection of poisonous traces |

Crowded environments are bus stations, buses, railway stations, trains, subways, markets, sports arenas, tourist attractions, shopping malls, universities, schools public office buildings and others. High risk facilities are airports and planes, power plans, sensitive government facilities, high risk factories, etc. Monitored objects may be peoples' body and clothing, cars, luggage, packages and cargo. The target substances to be detected may be substances in very low concentrations dissolved or suspended in water, whereupon the animals to be trained and used for detection may be fish.

While the invention has been described with respect to a preferred embodiment, it will be appreciated that this is set forth merely for purposes of example, and that many other variations, modifications and applications of the invention may be made.

What is claimed is:

1. A method of detecting a target substance in a monitored environment or object, comprising:
   (a) in a training phase, training at least one animal capable of detecting said target substance to execute a particular avoidance action, immediately upon detecting said target substance, in order to avoid a particular adverse stimulus;
   (b) in an operational phase, exposing said trained animal to a specimen of said monitored environment or object, and sensing when said animal has executed said particular avoidance action.

2. The method according to claim 1, wherein, in both the training phase and the operational phase, said animal is housed within a cage including the basic living necessities for the animal.

3. The method according to claim 2, wherein said particular adverse stimulus is an electrical, audible, visual, thermal, or mechanical stimulus which the animal naturally wishes to avoid.

4. The method according to claim 2, wherein said particular avoidance action is one which the animal would normally not perform when the target substance is not detected.

5. The method according to claim 4, wherein said particular avoidance action is to move to a section of the cage which is accessible to the animal only with some difficulty.

6. The method according to claim 2, wherein, during the operational phase, the target substance is occasionally injected into said cage to verify the ability of the animal to detect the target substance.

7. The method according to claim 6, wherein, during the operational phase, a neutral substance is occasionally injected into said cage to verify the ability of the animal to distinguish between neutral substances and the target substance.

8. The method according to claim 2, wherein, during the training phase, an alerting stimulus is produced immediately after the exposure of the animal to the target substance to alert the animal to the fact that a target substance was present.

9. The method according to claim 2, wherein, during the training phase, a "safety" stimulus is produced immediately after sensing said avoidance action.

10. The method according to claim 2, wherein, during at least said operational phase, the cage includes a plurality of animals each trained to detect a target substance.

11. The method according to claim 10, wherein at least one of said animals in the cage is trained to detect a different target substance from at least one other of said animals.

12. The method according to claim 10, wherein at least one of said animals in the cage is trained to perform a different avoidance action than at least one other of said animals.

13. The method according to claim 10, wherein a section of said cage is subjected to an arousing stimulus to arouse any of the animals occupying that section of the cage.

14. The method according to claim 1, wherein said animal is selected from the group consisting of rats, mice, dwarf hamsters, gerbils, shrews, dogs, monkeys, birds, insects and fish.

* * * * *